United States Patent [19]
Sanderson et al.

[11] Patent Number: 4,960,948
[45] Date of Patent: Oct. 2, 1990

[54] MANUFACTURE OF KETONE DERIVATIVES OF POLYOXYPROPYLENE GLYCOLS

[75] Inventors: John R. Sanderson, Leander; Edward T. Marquis, Austin, both of Tex.

[73] Assignee: Texaco Chemical Company, White Plains, N.Y.

[21] Appl. No.: 456,891

[22] Filed: Dec. 26, 1989

[51] Int. Cl.$^5$ .............................................. C07C 45/30
[52] U.S. Cl. ...................................... 568/405; 568/404
[58] Field of Search ................................. 568/405, 404

[56] References Cited

U.S. PATENT DOCUMENTS 2,983,759  5/1961  Matsumoto et al. ................ 568/405
4,141,919  2/1979  Gremmelmaier ................... 568/405

Primary Examiner—James H. Reamer
Attorney, Agent, or Firm—Jack H. Park; Kenneth R. Priem; Carl G. Ries

[57] ABSTRACT

Polyoxypropylene diketones are prepared by initially adding predetermined amounts of glacial acetic acid, a polyoxypropylene glycol and, optionally, water, to a reaction zone and thereafter adding an aqueous solution of an alkali metal or an alkaline earth metal hypochlorite oxidant to the reaction zone with agitation under reaction conditions including a temperature of about 10° to about 50° C., a pressure of about 0 to 1,000 psig. and a total reaction time of about 0.5 to 20 hours, whereby said polyoxypropylene glycol will be substantially selectively converted to the said corresponding diketone, and recovering said diketone.

13 Claims, No Drawings

MANUFACTURE OF KETONE DERIVATIVES OF POLYOXYPROPYLENE GLYCOLS

BACKGROUND OF THE INVENTION

1. Technical Field of the Invention

This invention relates to the preparation of ketone derivatives of polyoxypropylene glycols. More particularly, this invention relates to a method wherein the terminal hydroxyl groups of a polyoxypropylene glycol are oxidized to ketone groups. Still more particularly, this invention is directed to a method wherein a polyoxypropylene glycol is brought into contact with a hypochlorite oxidant in the presence of concentrated acetic acid in order to substantially selectively convert the hydroxyl groups of the polyoxypropylene glycol to terminal ketone groups. The ketone terminated derivatives of polyoxypropylene glycols are useful as intermediates for the preparation of a wide variety of products. For example, they may be reacted with amines to provide fuel additives or converted to carboxylic acids to provide surfactants.

2. Prior Art

It is known to react secondary alcohols and primary benzyl and allyl alcohols to the corresponding ketones and aldehydes in the presence of an oxidant such as $Cu(NO_3)_2$ or $Zn(NO_3)_2$ supported on silica gel in the presence of an aliphatic hydrocarbon solvent or a chlorinated aliphatic hydrocarbon solvent as shown, for example, by a paper by Takeshi Nishiguchi and Fumi Asano entitled "Oxidation of Alcohols by Metallic Nitrates Supported on Silica Gel" (J. Org. Chem. 1989, 54, 1531–1535).

Willis et al. U.S. Pat. No. 4,233,460 discloses a process for converting alkoxyalkanols to the corresponding acids by reacting the alcohol with an alkali metal hydroxide and a tertiary butyl hydroperoxide in the presence of a catalytic amount of palladium. The oxidation of polyethylene glycols to dicarboxylic acids is disclosed by Morris et al. in U.S. Pat. No. 4,256,916 wherein it is disclosed that polyethylene glycols can be converted to the corresponding carboxylic acids by oxidation in an aqueous solution over a fixed bed of a catalyst consisting of platinum on a granular carbon support.

Stutts et al. U.S. Pat. No. 4,488,944 discloses the preparation of dicarboxylic acids by the oxidation of polyalkylene glycols with electrochemically generated nickel-oxide hydroxide.

U.S. Pat. No. 3,479,403 to MacLean discloses that ruthenium can be used as an oxidation catalyst and that activity is enhanced by maintaining the oxidation potential of the ruthenium catalyst at less than the oxidizing potential of Ru(VIII) to greater than that of Ru(IV). In Example I, the oxidation of ethanol to acetic acid by the slow addition of an aqueous solution of calcium hypochlorite to an aqueous solution of ethanol containing a ruthenium chloride catalyst is disclosed. It is also disclosed in this example that the ruthenium chloride was oxidized to ruthenium tetraoxide. The oxidation of isopropanol to acetone with sodium hypochlorite in the presence of a ruthenium trichloride catalyst is also disclosed in Table II of the patent.

Barak et al. in a paper entitled "Selective Oxidation of Alcohols by a $H_2O_2$-$RuCl_3$ System under Phase-Transfer Conditions" (J. Org. Chem., 1988, Vol. 53, pp. 3553–3555) discloses in part that secondary alcohols can be oxidized to ketones with one hundred percent selectivity when using hydrogen peroxide as the oxidizing agent. Wolfe et al. disclose in an article entitled "Ruthenium Trichloride-catalysed Hypochlorite Oxidation of Organic Compounds" (Chemical Communications, 1970, pp. 1420–1421) disclose that in the catalytic hypochlorite oxidation of organic compounds with ruthenium trichloride, the ruthenium trichloride is oxidized to ruthenium tetraoxide.

A paper entitled "Fast and Selective Oxidation of Primary Alcohols to Aldehydes or to Carboxylic Acids and of Secondary Alcohols to Ketones Mediated by Oxoammonium Salts under Two-Phase Conditions" by Anelli et al. (J. Org. Chem., 1987, Vol. 52, pp. 2559–2562) discloses oxidation of a variety of alcohols in solution in methylene chloride with sodium hypochlorite.

In all of the prior art references (and in references not cited here) oxidation of polyoxyalkylene glycols has always been by oxidation of polyoxyethylene glycols. As far as we are aware, there are no references on the oxidation of a polyoxypropylene glycol to diketones. This is especially surprising in view of the fact that lower molecular weight secondary alcohols have been oxidized to ketones.

In copending Sanderson et al. U.S. patent application Ser. No. 444,211, filed 12/2/89, and entitled "Ketone Derivatives of Polyoxypropylene Glycols" (D#80,870), a process is disclosed wherein diketones are prepared by the oxidation of a polyoxypropylene glycol with an alkali metal or alkaline earth metal hypochlorite in the presence of a halogenated alkane solvent and a ruthenium catalyst.

SUMMARY OF THE INVENTION

It has been surprisingly discovered in accordance with the present invention that glacial acetic acid unexpectedly functions both as a solvent and a catalyst when a polyoxypropylene glycol feedstock of the present invention is oxidized with an alkali metal or alkaline earth metal hypochlorite. Thus, when the glacial acetic acid is used primarily as a solvent in the ratio of about 100 to about 500 parts by weight of glacial acetic acid per 100 parts by weight of polyoxypropylene glycol, it is not necessary to add another catalyst, such as a ruthenium catalyst.

It has been further discovered in accordance with the present invention that when only a catalytic amount of the glacial acetic acid is used (about 5 to about 100 parts by weight of glacial acetic acid per 100 parts by weight of polyoxypropylene glycol), it is not necessary to use an extraneous solvent such as a halogenated alkane solvent.

It has been still further discovered in accordance with the present invention that when only a catalytic amount of the glacial acetic acid is used (about 5 to about 100 parts by weight of glacial acetic acid per 100 parts by weight of polyoxypropylene glycol), there is an improvement in yield and selectivity to the diketone when water is added in the ratio of about 5 to about 100 parts by weight of water per 100 parts by weight of polyoxypropylene glycol and in the ratio of about 1 to about 3 parts of water per part of glacial acetic acid.

In accordance with the present invention, a polyoxyalkylene glycol having a molecular weight of about 200 to about 3,000 and having the formula:

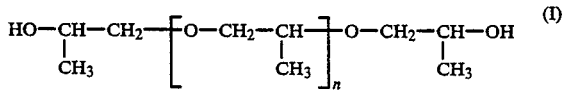

(I)

wherein n is a positive number having a value of 1 to about 50,
is oxidized in the presence of concentrated acetic acid with an alkali metal or alkaline earth metal hypochlorite at a temperature of about 10° to about 50° C. and a pressure of about 0 to 1,000 psig. over a period of about 0.5 to about 20 hours to provide the corresponding diketone having the formula:

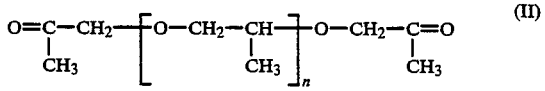

(II)

wherein n has the meaning given above.

The thus-prepared diketones are useful as intermediates for conversion to carboxylic acids to provide surfactants and for reaction with amine adducts to provide fuel additives, for example.

I

In accordance with a preferred embodiment of the present invention, a polyoxypropylene diketone having an average molecular weight of about 200 to about 3,000 is prepared by initially adding predetermined amounts of glacial acetic acid, a polyoxypropylene glycol and, optionally, water, to a reaction zone and by continuously adding an aqueous solution of an alkali metal or an alkaline earth metal hypochlorite oxidant to the reaction zone with agitation under reaction conditions including a temperature of about 10° to about 50° C., a pressure of about 0 to 1,000 psig. and a total reaction time of about 0.5 to 20 hours, whereby the polyoxypropylene glycol will be substantially selectively converted to the corresponding diketone, and recovering the diketone, the glacial acetic acid being added in the ratio of about 5 to about 500 parts by weight of glacial acetic acid per 100 parts by weight of said polyoxypropylene glycol, the water, when added, being added in the ratio of about 5 to about 100 parts by weight of water per 100 parts of polyoxypropylene glycol and in the ratio of about 1 to about 3 parts of water per part of glacial acetic acid, the aqueous solution of the hypochlorite containing from about 5 to about 25 wt. % of the alkali metal or alkaline earth metal hypochlorite and being slowly added to the reaction zone over a period of time of about 0.5 to 5 hours in an amount within the range from about 10 to about 100 parts by weight of the hypochlorite per 100 parts by weight of the polyoxypropylene glycol.

II

In accordance with another embodiment of the present invention, wherein only a catalytically effective amount of glacial acetic acid is used, the polyoxypropylene glycol and about 5 to about 100 parts by weight of glacial acetic acid per 100 parts by weight of polyoxypropylene glycol, are initially added to the reaction zone and the aqueous solution of alkali metal or alkaline earth metal hypochlorite oxidant is thereafter added to the reaction zone with agitation under the reaction conditions recited above to substantially selectively convert the polyoxypropylene glycol to the corresponding diketone, and the diketone is thereafter recovered from the reaction product.

III

In accordance with still another embodiment of the present invention, wherein a catalytically effective amount of glacial acetic acid is used and wherein a minor amount of water is added to the reaction zone to enhance the catalytic effectiveness of the glacial acetic acid, the polyoxypropylene glycol and about 5 to about 100 parts by weight of glacial acetic acid per 100 parts by weight of polyoxypropylene glycol, together with about 5 to about 100 parts by weight of water per 100 parts by weight of polyoxypropylene glycol and in the ratio of about 1 to about 3 parts of water per part of glacial acetic acid, are initially added to the reaction zone and the aqueous solution of alkali metal or alkaline earth metal hypochlorite oxidant is thereafter added to the reaction zone with agitation under the reaction conditions recited above to substantially selectively convert the polyoxypropylene glycol to the corresponding diketone, and the diketone is thereafter recovered from the reaction product,

DESCRIPTION OF THE PROCESS OF THE PRESENT INVENTION

The starting materials for the present invention include a polyoxypropylene glycol, as hereinafter defined, glacial acetic acid, an alkali metal or alkaline earth metal hypochlorite and, optionally, a minor amount of water.

The polyoxypropylene glycol feedstock to be used in accordance with the present invention is a polyoxypropylene glycol having an average molecular weight of about 200 to about 3,000 and having the formula:

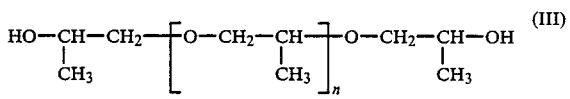

(III)

wherein n is a positive integer having a value of 1 to about 50.

The polyoxypropylene glycol feedstocks of the present invention are prepared commercially by reacting an initiator such as propylene glycol with an amount of propylene oxide sufficient to provide a polyoxypropylene glycol of the desired molecular weight. Since the addition of the propylene oxide is random, the final propoxylation product will not be a pure compound but, rather, will be a mixture of polyoxypropylene glycols. For example, if the amount of propylene oxide that is used is adequate to provide for a polyoxypropylene glycol having an average molecular weight of about 1,000, the final propoxylation product will actually be composed of a mixture of polyoxypropylene glycols having molecular weights varying from about 800 to about 1,200, the molecular weight distribution following a Gaussian distribution curve (sometimes referred to as a sine curve or a Poissan curve). As the average molecular weight of the polyoxypropylene glycol increases, the spread in molecular weight will also increase. Thus, when the average molecular weight of the polyoxypropylene glycol is 3,000, the deviation will be about 400 molecular weight units so that most of the product will fall within the molecular weight range of about 2,600 to about 3,400.

Also, the final propoxylation product will contain a minor amount of impurities (normally .5 wt. % or less) resulting, for example, from dehydration of terminal hydroxypropyl end groups which can occur to a limited extent at the reaction temperatures used during the propoxylation. A small portion of the feedstock will contain hydroxyethyl end groups.

Representative products of this nature include, for example, a polyoxypropylene glycol manufactured and sold by Texaco Chemical Company having an average molecular weight of about 230 (PPG-230), a polyoxypropylene glycol having an average molecular weight of about 400 (PPG-400) sold by the Texaco Chemical Company and a polyoxypropylene glycol having an average molecular weight of about 2,000 (PPG-2000) sold by the Texaco Chemical Company.

It is important to use glacial acetic acid in the practice of the present invention. Glacial acetic acid functions both as a solvent and as a catalyst. A controlled amount of water, within the range of about 1 to 3 parts of water per part of glacial acetic acid can be used to enhance the catalytic activity of the glacial acetic acid, but the use of larger amounts of water is deleterious.

The oxidant to be used in accordance with the present invention is an alkali metal or alkaline earth metal hypochlorite such as sodium hypochlorite, calcium hypochlorite, potassium hypochlorite, etc.

The hypochlorite oxidant is preferably employed in the form of 5 to 25 wt. % aqueous solution of the hypochlorite.

The Reaction Procedure

The reaction procedure to be used in practicing the process of the present invention is a procedure wherein the polyoxypropylene glycol, glacial acetic acid and water, if any, are added to a suitable reaction vessel, such as an autoclave, provided with appropriate agitation means and means for controlling temperature within the autoclave such as a jacket through which a heat exchange fluid may be circulated.

The hypochlorite oxidant is preferably employed in the form of 5 to 25 wt. % aqueous solution of the hypochlorite.

In practicing the process of the present invention, the polyoxypropylene glycol, glacial acetic acid, and water, if any, are initially added to a reaction zone and thereafter the aqueous solution of alkali metal or alkaline earth metal hypochlorite oxidant is slowly added to the reaction zone with agitation.

The reaction conditions to be employed include a temperature of about 10° to about 50° C. (and more preferably about 10° to about 30° C.), a pressure of about 0 to 1,000 psig. (preferably autogenous pressure) and a reaction time of about 0.5 to 20 hours, and more preferably about 0.5 to about 5 hours.

The oxidation reaction will be substantially complete at the end of the hypochlorite addition period, which will normally require from about 2 to about 5 hours, but since the oxidation reaction is a second order reaction, it will normally require about 15 to 20 hours of reaction at the indicated reaction temperature in order to bring the oxidation reaction to completion.

In general, the glacial acetic acid should be added to the reaction zone in the ratio of about 5 to about 500 parts by weight of glacial acetic acid per 100 parts by weight of the polyoxypropylene glycol.

When the glacial acetic acid is to be used primarily as a solvent, it should be added to the reaction zone in the ratio of about 100 to about 500 parts by weight of glacial acetic acid per 100 parts by weight of said polyoxypropylene glycol, and more preferably in the ratio of about 200 to about 300 parts by weight of glacial acetic acid per 100 parts by weight of said polyoxypropylene glycol.

When the glacial acetic acid is to be used primarily as a catalyst, it should be added to the reaction zone in the ratio of about 5 to about 100 parts by weight of glacial acetic acid per 100 parts by weight of polyoxypropylene glycol.

When water is to added to enhance the catalytic activity of the glacial acetic acid, the water should be added in the ratio of about 5 to about 100 parts by weight of water per 100 parts of polyoxypropylene glycol and in the ratio of about 1 to about 3 parts of water per part of glacial acetic acid.

The aqueous solution of alkali metal or alkaline earth metal hypochlorite should preferably contain from about 5 to about 25 wt. % of hypochlorite and the amount of the aqueous solution of the hypochlorite slowly added to said reaction zone should be an amount such that from about 10 to about 100 parts of hypochlorite is added to the reaction zone per 100 parts by weight of said polyoxypropylene glycol, and more preferably in the ratio of about 20 to about 50 parts by weight of hypochlorite per 100 parts of polyoxypropylene glycol.

At the end of the reaction, the polyoxypropylene diketone may be recovered from the reaction mixture in any suitable manner, such as by solvent extraction (e.g., solvent extraction with a chlorinated alkane such as trichlorethane, as shown in the examples, by extractive distillation, etc.

As a result, the polyoxypropylene glycol feedstock will be substantially selectively converted to the corresponding diketone derivative having the formula:

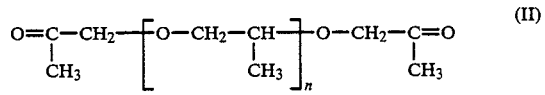
(II)

wherein n is a positive number having a value of 1 to about 50.

As indicated, the polyoxypropylene glycol feedstock comprises a mixture of polyoxypropylene glycols and minor amounts of other impurities. Thus, for example, although 95 wt. % or more of the polyoxypropylene glycol feedstock will contain terminal hydroxypropyl end groups that are substantially selectively oxidized to ketone end groups when using the process of the present invention, the feedstock will contain a small amount of feed components having terminal hydroxyethyl end groups. The hydroxyethyl end groups will normally be oxidized to carboxylic acid groups.

Also, the methylene group adjacent an ether group is susceptible to limited oxidation, i.e.

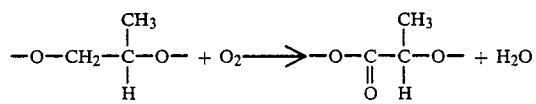

SPECIFIC EXAMPLES

The invention will be further illustrated by the following specific examples which are given by way of illustration and not as limitations on the scope of this invention.

Use of Glacial Acetic Acid as a Solvent 6528-3 - Procedure

Polypropylene glycol-2000 (50 g, Hydroxyl No. 55.7), and acetic acid (150 g) were charged to a 500 ml flask equipped with stirrer, water bath, thermometer, condenser and addition funnel. Sodium hypochlorite (74 g, 10%) was added dropwise over 0.5 hour. There was a mild exotherm but the temperature was maintained at 20°-25° C. by means of a water/ice bath. The reaction mixture was stirred for an additional 15 hours at 20°-25° C. The mixture was then poured into 500 ml water and the polyol extracted with 1,1,1-trichloroethane (3×100 ml). The trichlorethane was extracted (3×50 ml) 5% $NaHCO_3$ (1×50 ml) water. The organic solution was then dried over sodium sulfate and the solvent removed on a rotary evaporator. A clear liquid 45.0 g was obtained which had the following analytical results:

| Hydroxyl No.= | 42.6 meq/g |
|---|---|
| Acid No.= | 1.76 meq/g |
| Water= | 0.140 wt. % |

6528-4 - Scaleup

Polypropylene glycol-2000 (200 g, Hydroxyl No. 55.7), and acetic acid (400 g) were charged to a 1000 ml flask equipped with stirrer, water bath, thermometer, condenser, and addition funnel. 10% Sodium hypochlorite (600 g) was added dropwise over about 1 hour. There was a mild exotherm but the temperature was maintained at 20°-25° C. by means of a water bath. The reaction mixture was stirred for an additional 15 hours at 20°-25° C. The mixture was then poured into 1000 ml water and the polyol extracted with 1,1,1-trichlorethane (3×200 ml). The trichlorethane solution was extracted (3×100 ml) 5% $NaHCO_3$. The organic solution was then dried over anhydrous $Na_2SO_4$ and the solvent removed on a rotary evaporator (water bath 80° C., water aspirator). A clear, light-yellow liquid was obtained, 186.1 g, which had the following analytical results:

| Hydroxyl No.= | 12.6 meq/g |
|---|---|
| Acid No.= | 27.4 meq/g (due to acetic acid remaining) |
| Water= | 0.059 wt. % |

6495-4 - Comparison Example

Polypropylene glycol-2000 (100 g; Hydroxyl No. 55.7) was charged to a 100 ml flask with 100 ml water and 400 g 10% NaOCl. The mixture was heated slowly to 90°-100° C. and held at 92° C. for 5 hours. The reaction mixture was cooled to ambient temperature, 50 g conc. HCl added and the polyol extracted with methylene chloride (3×200 ml). The organic layer was washed with water (3×100 ml) and then dried over anhydrous $Na_2SO_4$. The solvent was removed on a rotary evaporator to give 95.2 g of clear, light yellow oil. The following analytical results were obtained:

| Hydroxyl No.= | 77.6 meq/g |
|---|---|
| Acid No.= | 11.4 meq/g |
| Water= | 0.013 wt. % |
| Carbonyl (by titration)= | <0.02% |

Use of Glacial Acetic Acid as a Catalyst

When the glacial acetic acid is used primarily as a catalyst, and only secondarily as a solvent, a higher conversion of the polyoxypropylene glycol is obtainable. This is illustrated by the examples that are summarized in Table I. Each of the examples of Table I was conducted in the manner described above for Example 6528-3.

TABLE I

OXIDATION OF POLYOXYPROPYLENE GLYCOLS USING CATALYTIC QUANTITIES OF GLACIAL ACETIC ACID

| Notebook Number | $PPG^a$ −2000 (g) | 10%[b] NaOCl (g) | $HOAC^c$ (g) | Time NaOCl Addn. (Hr.) | Reaction[d] Time (Hr.) | Temp. (°C.) | Hydroxyl No. mg/g | Acid No. mg/g | Water (wt. %) |
|---|---|---|---|---|---|---|---|---|---|
| 6528-3 | 50 | 74 | 150 | 0.5 | 15 | 20-25 | 42.6 | 1.76 | 0.140 |
| 6528-5 | 50 | 74 | 60 | 0.5 | 1 | 20-25 | 30.9 | 2.43 | 0.061 |
| 6528-6 | 50 | 74 | 30 | 0.5 | 2 | 20-25 | 17.3 | 1.23 | 0.024 |
| 6528-7 | 50 | 74 | 6 | 0.5 | 0.5 | 20-25 | 32.6 | 1.47 | 0.051 |
| 6528-9 | 50 | 100 | 5 | 1 | 0.5 | 20-35 | 16.4 | 5.65 | 0.022 |
| 6528-18 | 100 | 250 | 33 | 0.5 | 1 | 20-25 | 20.8 | 2.16 | 0.096 |
| 6528-19 | 100 | 250 | 20 | 1 | 2.2 | 20-25 | 14.3 | 1.89 | 0.158 |
| 6528-20 | 100 | 250 | 40 | 1 | 1 | 20-25 | 23.0 | 2.48 | 0.016 |

[a] Polypropylene glycol-2000 with Hydroxy No. 55.7.
[b] 10% NaOCl sold as swimming pool bleach.
[c] Glacial acetic acid 99%.
[d] Reaction time from end of NaOCl addition to workup.

Note from the results reported in Table I that as the amount of glacial acetic acid was progressively decreased in runs 6528-3, 6528-5, 6528-6, 6528-7, and 6528-9, there was a reduction in the hydroxyl number of the product and also a reduction in the acid number of the product. The decrease in hydroxyl number indicates that the conversion of the polyoxypropylene was increased and the decrease in the acid number indicates that there was improved selectivity to the ketone product, rather than to a carboxylic acid derivative.

A similar effect is noted in comparing Example 6528-30 with Example 6528-19 abd 6528-18.

Use of Water to Enhance the Catalytic Activity of Glacial Acetic Acid as a Catalyst When the catalytic activity of glacial acetic acid is enhanced by the addition of a controlled amount of water, a still higher conversion of the polyoxypropylene glycol is obtainable together with an enhanced selectivity. This is illustrated by the examples that are summarized in Table II. Each of the examples of Table II was conducted in the manner described below for Example 6528-78.

Procedure for 6528-78

PPG-1000 (1000 g), acetic acid (200 g) and water (400 g) were charged to a 5 l flask equipped with overhead stirrer, water bath, thermometer and addition funnel. 10% NaOCl (2000 g) was added slowly to the well-stirred reaction mixture. A mild exotherm was controlled by adding ice to the water bath from time to time. The temperature was maintained at 25° C.±5° C. The addition time of the NaOCl was 3.5 hours. The mixture was then stirred overnight (15 hours). The mixture was then poured into 1000 ml cyclohexane. Two layers formed an upper organic phase and a lower aqueous phase. The layers were separated and the aqueous phase extracted 2×200 ml cyclohexane. The combined organic extracts were extracted 1×200 ml H$_2$O, 2×200 ml 5% NaHCO$_3$. All aqueous extracts were discarded. The organic phase was dried over anhydrous Na$_2$SO$_4$ and the cyclohexane removed on a rotary evaporator (hot H$_2$O~80° C., water aspirator).

The very light yellow to white oil which remained was analyzed by titration (for OH # and acid #) and by carbon-13 and proton NMR.

OH # = 0.3 mg KOH/g
Acid # = 2.12 mg KOH/g

NMR analysis showed 85% of the termination was ketone, i.e.

NMR also indicated the presence of small quantities of acid and ester.

TABLE II
USE OF WATER TO ENHANCE CATALYTIC PROPERTIES OF GLACIAL ACETIC ACID IN THE OXIDATION OF POLYOXYPROPYLENE GLYCOLS

| Notebook Number | PPG- | (g) | 10% NaOCl (g) | H$_2$O (g) | HOAc (g) | Time Oxidant Addition (Hr.) | Reaction[a] Time (Hr.) | Temp. (C.) | Hydroxyl Number (mg/g) | Acid Number (mg/g) |
|---|---|---|---|---|---|---|---|---|---|---|
| 6528-71 | 1000 | 100 | 200 | 0 | 20 | 1.5 | 15 | 25 | 9.62 | 1.80 |
| 6528-73 | 1000 | 100 | 200 | 50 | 20 | 1.5 | 15 | 25 | 1.00 | 0.89 |
| 6528-76 | 1000 | 1000 | 2000 | 0 | 200 | 2.8 | 15 | 25 | 14.7 | 3.20 |
| 6528-78 | 1000 | 1000 | 2000 | 400 | 200 | 3.5 | 15 | 25 | 0.3** | 2.12 |
| 6528-86 | 400 | 600 | 2500 | 400 | 250 | 2.5 | 15 | 25 | 6.22 | 0.42 |
| 6528-54 | 1000 | 100 | 500 | 0 | 25 | 1.25 | 15 | 25 | 2.99 | 4.83 |
| 6528-56 | 600 | 60 | 500 | 0 | 20 | 0.5 | 15 | 25 | 33.7 | 12.9 |
| 6528-77 | 1000 | 100 | 200 | 40 | 20 | 1.3 | 20 | 25 | 16.8 | 1.47 |
| 6528-80 | 1000 | 100 | 200 | 30 | 20 | 3.0 | 20 | 25 | ~1 | 1.49 |

**NMR analysis indicated that 85% of the termination was ketone.
[a]Reaction time from end of NaOCl addition to workup.

Note from the results reported in Table II that the experiments conducted in the presence of water tended to provide reaction products having very low hydroxyl numbers and very low acid numbers.

Having thus described our invention, what is claimed is:

1. A method of making a polyoxypropylene diketone having an average molecular weight of about 200 to about 3,000 which comprises:

initially adding predetermined amounts of glacial acetic acid, a polyoxypropylene glycol and, optionally, water, to a reaction zone and thereafter adding an aqueous solution of an alkali metal or an alkaline earth metal hypochlorite oxidant to the reaction zone with agitation under reaction conditions including a temperature of about 10° to about 50° C., a pressure of about 0 to 1,000 psig. and a total reaction time of about 0.5 to 20 hours, whereby said polyoxypropylene glycol will be substantially selectively converted to the said corresponding diketone, and recovering said diketone, said glacial acetic acid being added in the ratio of about 5 to about 500 parts by weight of glacial acetic acid per 100 parts by weight of said polyoxypropylene glycol, said water, when added, being added in the ratio of about 5 to about 100 parts by weight of water per part 100 parts by weight of polyoxypropylene glycol and in the ratio of about 1 to about 3 parts of water per part of glacial acetic acid, said aqueous solution of said hypochlorite containing from about 5 to about 25 wt. % of said hypochlorite and being slowly added to said reaction zone over a period of about 0.5 to 5 hours in an amount of from about 10 to about 100 parts by weight of said hypochlorite per 100 parts by weight of said polyoxypropylene glycol, said polyoxypropylene diketone having the formula:

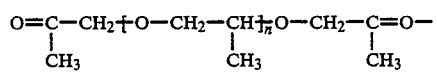

wherein n represents a positive number having a value of 1 to about 50.

2. A method as in claim 1 wherein the hypochlorite is an alkali metal hypochlorite.

3. A method as in claim 2 wherein the alkali metal hypochlorite is sodium hypochlorite.

4. A method as in claim 3 wherein only a polyoxypropylene glycol and glacial acetic acid are initially added to the reaction zone and wherein the glacial acetic acid is added in the ratio of about 100 to about 500 parts by weight of glacial acetic acid per 100 parts by weight of polyoxypropylene glycol.

5. A method as in claim 3 wherein only a polyoxypropylene glycol and a catalytic amount of glacial acetic acid are initially added to the reaction zone and wherein the glacial acetic acid is added in the ratio of about 5 to about 100 parts by weight of glacial acetic acid per 100 parts by weight of polyoxypropylene glycol.

6. A method as in claim 3, wherein a polyoxypropylene glycol, glacial acetic acid and water are initially added to the reaction zone, wherein the glacial acetic acid is added in the ratio of about 5 to about 100 parts by weight of glacial acetic acid per 100 parts by weight of polyoxypropylene glycol, and wherein the water is added in the ratio of about 5 to about 100 parts by weight of water per 100 parts by weight of polyoxypropylene glycol and in the ratio of about 1 to about 3 parts of water per part of glacial acetic acid.

7. A method as in claim 3 wherein the polyoxypropylene glycol added to the reaction zone is a polyoxypropylene glycol having an average molecular weight of about 400 and wherein n in the formula of claim 1 represents a number having an average value of about 5.

8. A method as in claim 3 wherein the polyoxypropylene glycol added to the reaction zone is a polyoxypropylene glycol having an average molecular weight of about 600 and wherein n in the formula of claim 1 represents a number having an average value of about 8.

9. A method as in claim 3 wherein the polyoxypropylene glycol added to the reaction zone is a polyoxypropylene glycol having an average molecular weight of about 1,000 and wherein n in the formula of claim 1 represents a number having an average value of about 15.

10. A method of making a polyoxypropylene diketone having an average molecular weight of about 200 to about 3,000 which comprises:

initially adding predetermined amounts of glacial acetic acid, a polyoxypropylene glycol and water, to a reaction zone and thereafter adding an aqueous solution of sodium hypochlorite to the reaction zone with agitation under reaction conditions including a temperature of about 10° to about 30° C., atmospheric pressure and a total reaction time of about 0.5 to 5 hours, whereby said polyoxypropylene glycol will be substantially selectively converted to the said corresponding diketone, and recovering said diketone, said glacial acetic acid being added in the ratio of about 10 to about 60 parts by weight of glacial acetic acid per 100 parts by weight of said polyoxypropylene glycol, said water being added in the ratio of about 30 to about 50 parts by weight of water per 100 parts by weight of polyoxypropylene glycol and in the ratio of about 1 to about 3 parts of water per part of glacial acetic acid, said aqueous solution of said hypochlorite containing from about 5 to about 25 wt. % of said hypochlorite and being slowly added to said reaction zone over a period of about 1 to about 3 hours in an amount of from about 20 to about 50 parts by weight of said hypochlorite per 100 parts by weight of said polyoxypropylene glycol, said polyoxypropylene diketone having the formula:

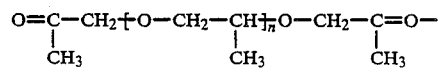

wherein n in said formula represents a positive number having a value of 1 to about 50.

11. A method as in claim 10 wherein the polyoxypropylene glycol added to the reaction zone is a polyoxypropylene glycol having an average molecular weight of about 400 and wherein n in the formula of claim 10 represents a number having an average value of about 5.

12. A method as in claim 10 wherein the polyoxypropylene glycol added to the reaction zone is a polyoxypropylene glycol having an average molecular weight of about 600 and wherein n in the formula of claim 10 represents a number having an average value of about 8.

13. A method as in claim 10 wherein the polyoxypropylene glycol added to the reaction zone is a polyoxypropylene glycol having an average molecular weight of about 2,000 and wherein n in the formula of claim 10 represents a number having an average value of about 32.

* * * * *